United States Patent [19]

Rody

[11] 4,293,468
[45] Oct. 6, 1981

[54] MALONATE DERIVATIVES AS STABILIZERS FOR ORGANIC MATERIALS

[75] Inventor: Jean Rody, Basel, Switzerland

[73] Assignee: Ciba-Geigy AG, Basel, Switzerland

[21] Appl. No.: 118,219

[22] Filed: Feb. 4, 1980

Related U.S. Application Data

[63] Continuation of Ser. No. 958,447, Nov. 7, 1978, abandoned, which is a continuation of Ser. No. 792,179, Apr. 29, 1977, abandoned.

[30] Foreign Application Priority Data

May 4, 1976 [CH] Switzerland ............................ 5558/76

[51] Int. Cl.³ .................... C08K 5/34; C07D 401/12
[52] U.S. Cl. ............................ 260/45.8 N; 542/427; 546/187; 546/188; 546/216; 546/221
[58] Field of Search ................ 260/45.8 N, 45.8 NZ; 542/427; 546/187, 188

[56] References Cited

U.S. PATENT DOCUMENTS 3,640,928  2/1972  Murayama et al. ............ 546/188 X
3,993,655 11/1976  Rasberger et al. ............ 546/188 X
4,021,432  5/1977  Holt et al. ................... 546/188 X
4,056,507 11/1977  Ramey et al. ................. 260/45.8 N

FOREIGN PATENT DOCUMENTS 4643302 12/1971 Japan ............................. 546/188

Primary Examiner—Richard A. Schwartz
Attorney, Agent, or Firm—Wenderoth, Lind & Ponack

[57] ABSTRACT

Malonates of the formula I

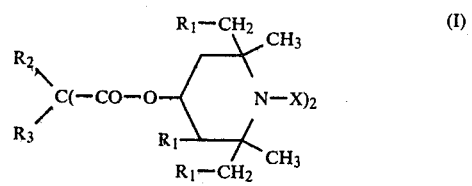

in which $R_1$ is hydrogen or $C_1$-$C_4$-alkyl, $R_2$ is $C_1$-$C_{12}$-alkyl, $C_3$-$C_4$-alkenyl, benzyl or phenyl which is optionally substituted by $C_1$-$C_8$-alkyl or $C_1$-$C_8$-alkoxy, or is cyano, $R_3$ is $C_1$-$C_{12}$-alkyl, $C_3$-$C_4$-alkenyl or benzyl and X denotes hydrogen, oxyl, $C_1$-$C_{12}$-alkyl, $C_3$-$C_6$-alkenyl, $C_3$-$C_4$-alkinyl, $C_2$-$C_{21}$-alkoxyalkyl, $C_7$-$C_8$-aralkyl, 2,3-epoxypropyl, an aliphatic acyl group with 1-4 C atoms or one of the groups —$CH_2COOR_4$, —$CH_2$—$CH(R_5)$—$OR_6$, —$COOR_7$ or —$CONHR_7$, in which $R_4$ is $C_1$-$C_8$-alkyl, $C_3$-$C_6$-alkenyl, phenyl, $C_7$-$C_8$-aralkyl or cyclohexyl and $R_5$ is hydrogen, methyl or phenyl and $R_6$ denotes hydrogen or an aliphatic or aromatic, araliphatic or alicyclic acyl group with 1-18 C atoms, in which the aromatic part can optionally be substituted by chlorine, $C_1$-$C_4$-alkyl or $C_1$-$C_8$-alkoxy and/or by hydroxyl, and $R_7$ is $C_1$-$C_{12}$-alkyl, cyclohexyl, phenyl or benzyl as stabilizer for organic polymers.

16 Claims, No Drawings

MALONATE DERIVATIVES AS STABILIZERS FOR ORGANIC MATERIALS

This is a continuation of application Ser. No. 958,447, filed Nov. 7, 1978, now abandoned, which in turn is a continuation of application Ser. No. 792,179 filed Apr. 29, 1977, now abandoned.

The present invention relates to new malonates, processes for their manufacture and their use as stabilisers and to organic material which, with the aid of these compounds, has been stabilised against light-induced degradation.

Malonates of sterically hindered 4-hydroxy-piperidines are known as stabilisers for synthetic polymers from U.S. Pat. No. 3,640,928 and British Patent Specification No. 1,399,239. These stabilisers have properties, for example with regard to the stability to hydrolysis, the volatility, stability to extraction and stability to exudation, which prove troublesome in industrial use. Furthermore, sterically hindered hydroxybenzyl-malonates of sterically hindered 4-hydroxy-piperidines are known as stabilisers for synthetic polymers from German Offenlegungsschrift No. 2,456,864. However, when these stabilisers are used in practice, discolorations, which are frequently undesired, arise when the compounds are subjected to excessive heat, which can arise even unintentionally during incorporation or processing, or, say, when mixing in, as a melt, via a screw into the extruder.

Starting from this state of the art, it was the object of the invention to provide stabilisers for organic materials which do not have the disadvantages of the stabilisers known hitherto or have the disadvantages only to a substantially lesser extent.

The invention relates to malonates of the formula I

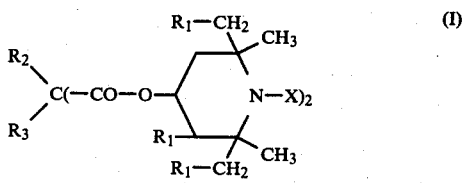

in which $R_1$ is hydrogen or $C_1$–$C_4$-alkyl, $R_2$ is $C_1$–$C_{12}$-alkyl, $C_3$–$C_4$-alkenyl, benzyl or phenyl which is optionally substituted by $C_1$–$C_8$-alkyl or $C_1$–$C_8$-alkoxy, or is cyano, $R_3$ is $C_1$–$C_{12}$-alkyl, $C_3$–$C_4$-alkenyl or benzyl and X denotes hydrogen, oxyl, $C_1$–$C_{12}$-alkyl, $C_3$–$C_6$-alkenyl, $C_3$–$C_4$-alkinyl, $C_2$–$C_{21}$-alkoxyalkyl, $C_7$–$C_{11}$-aralkyl, 2,3-epoxypropyl, an aliphatic acyl group with 1–4 C atoms or one of the groups —$CH_2COOR_4$, —$CH_2$—$CH(R_5)$—$OR_6$, —$COOR_7$ or —$CONHR_7$, in which $R_4$ is $C_1$–$C_8$-alkyl, $C_3$–$C_6$-alkenyl, phenyl, $C_7$–$C_8$-aralkyl or cyclohexyl and $R_5$ is hydrogen, methyl or phenyl and $R_6$ denotes hydrogen or an aliphatic or aromatic, araliphatic or alicyclic acyl group with 1–18 C atoms, in which the aromatic part can optionally be substituted by chlorine, $C_1$–$C_4$-alkyl or $C_1$–$C_8$-alkoxy and/or by hydroxyl, and $R_7$ is $C_1$–$C_{12}$-alkyl, cyclohexyl, phenyl or benzyl.

As $C_1$–$C_4$-alkyl, $R_1$ is branched or, in particular, unbranched alkyl, such as ethyl, n-propyl or n-butyl, but above all methyl. $R_1$ is preferably hydrogen. All the substituents $R_1$ are identical.

As $C_1$–$C_{12}$-alkyl, $R_2$, or $R_3$, is branched or unbranched alkyl, especially branched or unbranched alkyl with 2–8 C atoms, such as ethyl, n- or i-propyl, n- or i-butyl or a pentyl, hexyl, heptyl or octyl, such as n- or i-octyl.

As $C_3$–$C_4$-alkenyl, $R_2$, or $R_3$, is in particular methallyl and above all allyl.

As phenyl which is substituted by $C_1$–$C_8$-alkyl, $R_2$ is, in particular, phenyl which is substituted by ethyl or n- or i-propyl but above all by methyl and as phenyl which is substituted by $C_1$–$C_8$-alkoxy $R_2$ is phenyl which is substituted by ethoxy or n- or i-propoxy but above all by methoxy. However, phenyl $R_2$ is preferably unsubstituted.

If $R_2$ and $R_3$ are alkyl they should not both contain a tertiary $\alpha$-C atom at the same time. Thus, when $R_2$ and $R_3$ are alkyl, at least one of them is alkyl containing a primary or secondary $\alpha$-C atom.

As $C_1$–$C_{12}$-alkyl, X is, for example, methyl, ethyl, n-propyl, n-butyl, n-pentyl, n-hexyl, n-octyl, n-decyl or n-dodecyl. Alkyl groups with 1–8 C atoms, especially those with 1–4 C atoms and above all methyl are preferred.

As $C_3$–$C_6$-alkenyl, X is, for example, allyl, 2-butenyl or 2-hexenyl, especially allyl.

As $C_3$–$C_4$-alkinyl, X is, for example, propargyl.

If X denotes $C_2$–$C_{21}$-alkoxyalkyl, the alkyl part can contain 1–3 C atoms and the alkoxy part can consist of 1–18 C atoms, such as in, for example, methoxymethyl, ethoxymethyl, 2-methoxyethyl, 2-ethoxyethyl, 2-n-butoxyethyl, 3-n-butoxypropyl, 2-octoxyethyl or 2-octadecyloxyethyl. Compounds in which X denotes an alkoxyalkyl group with 2–6 C atoms are to be mentioned in particular.

As $C_7$–$C_{11}$-aralkyl, X is, for example, benzyl or $\alpha$-phenylethyl, or benzyl substituted by $C_1$–$C_4$-alkyl, such as methylbenzyl or tert.-butylbenzyl, e.g. 4-tert.-butylbenzyl.

As an aliphatic acyl group with 1–4 C atoms, X is, for example, formyl, acetyl, acryloyl or crotonyl, especially acetyl.

If X is the group —$CH_2COOR_4$, $R_4$, as $C_1$–$C_{12}$-alkyl, denotes, for example, methyl, ethyl, isopropyl, n-butyl, isobutyl, t-butyl, isopentyl, n-octyl, n-decyl or n-dodecyl. $R_4$ is preferably $C_1$–$C_4$-alkyl. As $C_3$–$C_6$-alkenyl, $R_4$ is, for example, allyl, 2-butenyl or 2-hexenyl. As $C_7$–$C_8$-aralkyl, $R_4$ is, for example, benzyl or $\alpha$-phenylethyl.

If X is the group —$CH_2$—$CH(R_5)$—$OR_6$, $R_5$ denotes hydrogen, methyl or phenyl, especially hydrogen. As an aliphatic, aromatic, alicyclic or araliphatic $C_1$–$C_{18}$-acyl radical which is optionally substituted in the aromatic part by chlorine or $C_1$–$C_4$-alkyl, such as methyl, ethyl, n-propyl or t-butyl, or by $C_1$–$C_8$-alkoxy, such as methoxy, ethoxy, butoxy or octoxy, and/or by hydroxyl, $R_6$ is, for example, acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, $\beta$-(3,5-di-t-butyl-4-hydroxyphenyl)-propionyl, phenylacetyl, cinnamoyl or hexahydrobenzoyl.

If X is the group —$COOR_7$, $R_7$, as $C_1$–$C_{12}$-alkyl, is, for example, methyl, ethyl, isobutyl, n-hexyl, n-octyl, n-decyl or n-dodecyl. Alkyl groups with 1–4 C atoms are preferred as $R_7$. The same applies to $R_7$ in —$CONHR_7$.

Malonates Ia of the formula I in which $R_1$ is hydrogen or methyl, $R_2$ is $C_2$–$C_8$-alkyl, allyl, methallyl, benzyl or phenyl, $R_3$ is $C_2$–$C_8$-alkyl, allyl, methallyl or benzyl and X is hydrogen, oxyl, $C_1-C_8$-alkyl, $C_3-C_4$-alkenyl or alkinyl, $C_2-C_6$-alkoxyalkyl, $C_7-C_8$-aralkyl, acetyl, acryloyl or crotonyl or denotes one of the groups $-CH_2-COOR_4$, $-CH_2-CH(R_5)-OR_6$, $-COOR_7$ or $-CONHR_7$, in which $R_4$ is $C_1-C_4$-alkyl, $C_3-C_4$-alkenyl, phenyl, $C_7-C_8$-aralkyl or cyclohexyl and $R_5$ is hydrogen, methyl or phenyl and $R_6$ denotes hydrogen or an aliphatic, aromatic, alicyclic or araliphatic acyl group with 1-18 C atoms, in which the aromatic part can optionally be substituted by chlorine, $C_1-C_4$-alkyl, $C_1-C_8$-alkoxy and/or hydroxyl, and $R_7$ is $C_1-C_{12}$-alkyl are preferred.

Malonates Ib of the formula I in which $R_1$ is hydrogen or methyl, $R_2$ is $C_1-C_8$-alkyl, allyl, methallyl, benzyl or phenyl, $R_3$ is $C_2-C_8$-alkyl or benzyl and X is hydrogen, $C_1-C_4$-alkyl, allyl, benzyl, $C_2-C_6$-alkoxyalkyl, acetyl, acryloyl or crotonyl or one of the groups $-CH_2-COOR_4$, $-CH_2-CH(R_5)-OR_6$, $-COOR_7$ or $-CONHR_7$, in which $R_4$ is $C_1-C_4$-alkyl and $R_5$ denotes hydrogen or methyl and $R_6$ denotes hydrogen and $R_7$ is $C_1-C_4$-alkyl, are particularly preferred.

The invention relates above all to malonates Ic of the formula I in which $R_1$ is hydrogen or methyl, $R_2$ is $C_1-C_6$-alkyl, allyl, methallyl or benzyl, $R_3$ is benzyl and X is hydrogen, methyl, allyl, benzyl or acetyl.

In the above malonates I and Ia-Ic, $R_2$ and $R_3$ are preferably benzyl. Furthermore, $R_1$ is preferably hydrogen. X is preferably methyl or, in particular, hydrogen.

Examples of malonates of the formula I can be seen from the illustrative examples. These malonates are particularly preferred, and also the following:
(1) bis-(2,2,6,6-tetramethyl-4-piperidinyl) dimethallylmalonate, (2) bis-(1,2,2,6,6-pentamethyl-4-piperidinyl) dimethallylmalonate, (3) bis-(1-allyl-2,2,6,6-tetramethyl-4-piperidinyl) diallylmalonate, (4) bis-(2,2,6,6-tetramethyl-4-piperidinyl) ethyl-benzyl-malonate, (5) bis-(2,2,6,6-tetramethyl-4-piperidinyl) n-octyl-benzyl-malonate, (6) bis-(1,2,2,6,6-pentamethyl-4-piperidinyl) n-octyl-benzyl-malonate, (1) bis-(2,2,6,6-tetramethyl-4-piperidinyl) allyl-benzyl-malonate, (8) bis-(1,2,2,6,6-pentamethyl-4-piperidinyl) allyl-benzyl-malonate, (9) bis-(1-allyl-2,2,6,6-tetramethyl-4-piperidinyl) allyl-benzyl-malonate, (10) bis-[1-(2,3-epoxypropyl)-2,2,6,6-tetramethyl-4-piperidinyl] dibenzylmalonate, (11) bis-[1-(2,3-epoxypropyl)-2,2,6,6-tetramethyl-4-piperidinyl] diethylmalonate, (12) bis-(1-n-octyl-2,2,6,6-tetramethyl-4-piperidinyl) dimethylmalonate, (13) bis-(2,2,6,6-tetramethyl-4-piperidinyl) ethyl-phenyl-malonate, (14) bis-(1,2,2,6,6-pentamethyl-4-piperidinyl) allyl-phenyl-malonate, (15) bis-(2,2,6,6-tetramethyl-4-piperidinyl) benzylphenyl-malonate, (16) bis-(2,3,6-trimethyl-2,6-diethyl-4-piperidinyl) dibenzylmalonate, (17) bis-(1,2,3,6-tetramethyl-2,6-diethyl-4-piperidinyl) dibenzylmalonate, (18) bis-(2,3,6-trimethyl-2,6-diethyl-4-piperidinyl) ethyl-benzyl-malonate, (19) bis-(1,2,3,6-tetramethyl-2,6-diethyl-4-piperidinyl) allylbenzyl-malonate, (20) bis-(1-octyl-2,2,6,6-tetramethyl-4-piperidinyl) dibenzylmalonate, (21) bis-(1-octyl-2,2,6,6-tetramethyl-4-piperidinyl) diethylmalonate, (22) bis-[1-(2-hydroxyethyl)-2,2,6,6-tetramethyl-4-piperidinyl] dibenzylmalonate, (23) bis-[1-(2-hydroxyethyl)-2,2,6,6-tetramethyl-4-piperidinyl] diethylmalonate, (24) bis-[1-(2-hydroxypropyl)-2,2,6,6-tetramethyl-4-piperidinyl] dibenzylmalonate, (25) bis-[1-(2-hydroxypropyl)-2,2,6,6-tetramethyl-4-piperidinyl] diethylmalonate, (26) bis-(1-dodecyl-2,2,6,6-tetramethyl-4-piperidinyl) dibenzylmalonate, (27) bis-(1-dodecyl-2,2,6,6-tetramethyl-4-piperidinyl) diethylmalonate.

The compounds of the formula I can be manufactured by various methods which consist of several individual steps in various sequences. The individual steps consist of reactions which are known, above all those known from the chemistry of malonic acid derivatives.

The synthesis can start with the conversion of a lower alkyl malonate, such as, for example, diethyl malonate, into the corresponding bis-piperidinyl malonate III by transesterification with a 4-piperidinol of the formula II.

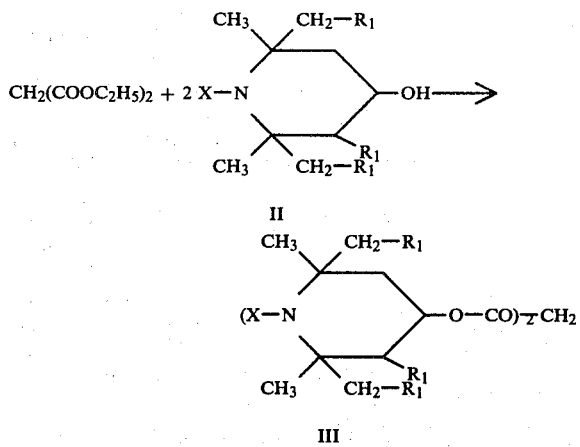

In this reaction, X can already be the substituent desired in the compound of the formula I; alternatively, the tetramethylpiperidinol which is unsubstituted on the nitrogen (II, X=H) is used and the substituent X is introduced after the transesterification or in a later stage of the synthesis route.

X can be introduced by the customary methods for N-alkylation and N-acylation, for example by reaction with alkyl halides, alkenyl halides, propargyl chloride, benzyl chloride or carboxylic acid chlorides, preferably in the presence of molar amounts of a base.

An N-acylation can also be carried out with carboxylic acid anhydrides, for example with acetic anhydride. Hydroxyalkyl radicals are introduced by reaction with epoxides, for example ethylene oxide or propylene oxide, and can be converted into the corresponding N-acyloxyalkyl groups by reaction with carboxylic acid chlorides or carboxylic acid anhydrides. N-oxyls (X=—O.) can be manufactured from the NH compounds by oxidation with per-acids or hydrogen peroxide.

As the next step, either first the substituent $R_2$ and then $R_3$, or first the substituent $R_3$ and then $R_2$, can be introduced into the compounds of the formula III.

The radical $R_2$ can be introduced in the manner of a malonate synthesis by first converting the ester III, by reaction with one equivalent of an alkali metal, an alkali metal alcoholate, an alkali metal amide or an alkali metal hydride or of a similar basic alkali metal compound, into the alkali metal compound of III and then reacting the latter with 1 mol of an $R_2$ halide $R_2Hal$ (Hal=Cl, Br or I) in the customary manner.

The substituent $R_3$ subsequently has to be introduced into this $R_2$-malonate. However, if $R_2$ is identical to $R_3$, both radicals can advantageously be introduced at the same time.

The introduction of the substituents $R_3$ can be effected by the classical method of the C-alkylation of malonates, the $R_2$-malonate first being converted into its alkali metal compound and then being reacted with a halogen compound $R_3$Hal. In this case Hal again denotes Cl, Br or I. Approximately 1 mol of a monohalide $R_3$Hal is used per mol of alkali metal compound. Examples of such monohalides are alkyl halides, alkenyl halides or benzyl halides.

Finally, X can also be introduced at the same time as $R_3$ is introduced if X and $R_3$ are identical, for example when they denote alkyl, alkenyl or benzyl.

Because of these numerous possibilities for carrying out the individual reaction steps, that is to say the introduction of the piperidinyl radical, the introduction of the group $R_2$, the introduction of the group $R_3$ and, optionally, the introduction of X, the sequence of the individual steps will be chosen in the manner which seems most appropriate in a particular case.

The above reaction of a lower alkyl malonate with a 4-piperidinol of the formula II can also advantageously be carried out with a malonate which is substituted in the $\alpha$-position by $R_2$ and $R_3$ and in this case the procedure is, in particular, as described above for a malonate plus 4-piperidinol.

The starting materials are known or, if they are new, can be manufactured according to methods which are in themselves known and analogously to known compounds. Thus, the 4-hydroxypiperidines II can be manufactured from the corresponding 4-oxopiperidines by reduction, for example by catalytic hydrogenation over Raney nickel.

The 4-oxopiperidines in which X is hydrogen can be manufactured by various processes.

Thus, for example, the reaction of an aliphatic ketone with ammonia is described by W. Traube in Chem. Ber. 41, 777 (1908).

4-Oxopiperidines in which X denotes hydrogen can also be manufactured analogously to the process described in U.S. Pat. No. 3,513,170. In this reaction, a tetrahydropyrimidine which is substituted by alkyl is rearranged by hydrolysis in the presence of an acid catalyst.

1-H-4-Oxopiperidines which possess substituents of different types in the 2-position and the 6-position can be manufactured by reacting a ketone of the formula $R_1$—$CH_2$—CO—$CH_3$ with ammonia. The pyrimidine formed is hydrolysed as described in Helv. Chim. Acta 30, 114 (1947) to give an aminoketone. This is reacted, in a second process step, with ammonia and a ketone $R_1$—$CH_2$—CO—$CH_3$, as is described, for example, in Monatsh. Chemie 88, 464 (1957). The 4-oxo-piperidines in which X is hydrogen can be obtained from the pyrimidine, which results from this reaction, by hydrolysis.

According to the present invention, the compounds of the formula I can be used as stabilisers for plastics, to protect them against damage due to the action of oxygen, heat and light. Examples of such plastics are the polymers listed on pages 12–14 of German Offenlegungsschrift No. 2,456,864.

The stabilisation of polyolefines and styrene polymers and of polyurethanes is of particular importance and the malonates of the formula I are outstandingly suitable for this. Examples of such polymers are high density polyethylene and low density polyethylene, polypropylene, ethylene-propylene copolymers, polystyrene, styrene-butadiene-acrylonitrile copolymers, mixtures of polyolefines or of styrene polymers and polyurethanes based on polyethers or polyesters, in the form of lacquers, elastomers or foams.

The stabilisers are added to the plastics in a concentration of 0.01 to 5% by weight, calculated relative to the material to be stabilised. Preferably, 0.03 to 1.5, and particularly preferentially 0.2 to 0.6, % by weight of the compounds, calculated relative to the material to be stabilised, are incorporated into the latter.

Incorporation can be effected after polymerisation, for example by mixing the compounds, and optionally further additives, into the melt by the methods customary in the art, before or during shaping, or by applying the dissolved or dispersed compounds to the polymer, if necessary with subsequent evaporation of the solvent.

The new compounds can also be added to the plastics to be stabilised in the form of a master batch which contains these compounds, for example in a concentration of 2.5 to 25% by weight.

In the case of crosslinked polyethylene, the compounds are added prior to crosslinking.

In addition to the compounds of the formula I, yet further known stabilisers can also be added to the plastics. These stabilisers can be, for example, antioxidants, light protection agents or metal deactivators, or costabilisers, such as, for example, those of the phosphorous acid ester type. Furthermore, other additives customary in plastics technology, such as, for example, flameproofing agents, antistatic agents, plasticisers, lubricants, blowing agents, pigments, reinforcing materials or fillers can be added.

The invention therefore also relates to plastics stabilised by the addition of 0.01 to 5% by weight of a compound of the formula I, which plastics optionally can contain yet further known and customary additives. The plastics stabilised in this way can be used in very diverse forms, for example as sheets, fibres, tapes or profiles, or as binders for lacquers, adhesives or putties.

The manufacture and use of the compounds according to the invention is described in more detail in the examples which follow. In these examples parts denote parts by weight and % denotes percentages by weight. The temperatures are given in degrees centigrade.

EXAMPLE 1

After adding 1 g of lithium amide, 188.2 g of dimethyl diethylmalonate and 320 g of 2,2,6,6-tetramethyl-4-hydroxypiperidine in 200 ml of ligroin are warmed to about 120° under a gentle stream of nitrogen. The methanol formed during the transesterification is distilled off continuously. The reaction has virtually ended after about 6 hours. The reaction mixture is diluted with 100 ml of ligroin and extracted three times at 80° with, in each case, 100 ml of hot water. Bis(2,2,6,6-tetramethyl-4-piperidinyl) diethylmalonate (compound 1), which has a melting point of 90°, crystallises when the ligroin solution cools.

EXAMPLES 2–6

If there is used, instead of dimethyl diethylmalonate according to Example 1, an equivalent amount of diethyl di-n-butylmalonate or of dimethyl di-isobutylmalonate or of diethyl diallylmalonate or of dimethyl dibenzylmalonate or of dimethyl n-butyl-benzylmalonate, with the procedure otherwise as described in Example 1, there are obtained after corresponding processing: bis-(2,2,6,6-tetramethyl-4-piperidinyl) di-n-butylmalonate (compound 2) as an almost colourless oil (molecular distillation at 120°/0.005 mm Hg) or bis-(2,2,6,6-tetramethyl-4-piperidinyl) diisobutylmalonate (compound 3) having a melting point of 81°–83° or bis- (2,2,6,6-tetramethyl-4-piperidinyl) diallylmalonate (compound 4) having a melting point of 84°–87° or bis-(2,2,6,6-tetramethyl-4-piperidinyl) dibenzylmalonate (compound 5) having a melting point of 128°–130° or bis-(2,2,6,6-tetramethyl-4-piperidinyl) n-butyl-benzylmalonate (compound 6) having a melting point of 87°–88°, respectively.

EXAMPLE 7

205 g of bis-(1,2,2,6,6-pentamethyl-4-piperidinyl) malonate, prepared according to known methods, are heated with 12 g of sodium hydride in 500 ml of absolute toluene for 6 hours under reflux. After this time the evolution of hydrogen has ceased and virtually no particles of sodium hydride can be detected in the reaction mixture. The mixture is cooled to 50°, 63 g of benzyl chloride are added dropwise in about 30 minutes and the mixture is then stirred for 1 hour under reflux. It is then again cooled to about 50°, a further 12 g of sodium hydride are added and the mixture is heated under reflux until the evolution of hydrogen has completely ceased (about 6 hours). It is then again cooled to 50°, 63 g of benzyl chloride are added dropwise in about 30 minutes and the mixture is then stirred for 3 hours under reflux. The reaction solution is washed with three times 200 ml of water, dried over sodium sulphate and evaporated. Crystallisation of the residue from hexane gives bis-(1,2,2,6,6-pentamethyl-4-piperidinyl) dibenzylmalonate (compound 7) which has a melting point of 121°–122°.

EXAMPLES 8–9

If the equivalent amount of ethyl iodide and allyl chloride is used instead of benzyl chloride according to Example 7, with the procedure otherwise being as described in Example 7, the compounds obtained are bis-(1,2,2,6,6-pentamethyl-4-piperidinyl) diethylmalonate (compound 8) having a melting point of 71° and bis-(1,2,2,6,6-pentamethyl-4-piperidinyl) diallylmalonate (compound 9) having a melting point of 100°–101°, respectively.

EXAMPLE 10

115.9 g of bis-(1-allyl-2,2,6,6-tetramethyl-4-piperidinyl) malonate, produced according to known methods, are refluxed for 6 hours with 6 g of sodium hydride in 300 ml of absolute toluene. The reaction mixture is cooled to 50°; 31.5 g of benzyl chloride are added dropwise in about 20 minutes and stirring is subsequently maintained for 1 hour under reflux. The temperature afterwards is again lowered to about 50°; a further 6 g of sodium hydride are added and the mixture is refluxed until the evolution of hydrogen has ceased completely (about 6 hours). The mixture is again cooled to 50°; a dropwise addition of 31.5 g of benzyl chloride is made in the course of about 20 minutes, and stirring under reflux is then carried out for 2 hours. The reaction solution is washed three times with 150 ml of water each time, dried over sodium sulphate and concentrated by evaporation. Crystallisation of the residue from hexane yields bis-(1-allyl-2,2,6,6-tetramethyl-4-piperidinyl) dibenzylmalonate (compound 10), m.p. 120°–121°.

EXAMPLES 11–17

If, instead of bis-(1-allyl-2,2,6,6-tetramethyl-4-piperidinyl) malonate, there is used with the procedure otherwise as described in Example 10 an equivalent amount of bis-(1-benzyl-2,2,6,6-tetramethyl-4-piperidinyl) malonate and bis-(1-propyl-2,2,6,6-tetramethyl-4-piperidinyl) malonate and bis-(1-butyl-2,2,6,6-tetramethyl-4-piperidinyl) malonate and bis-(1-hexyl-2,2,6,6-tetramethyl-4-piperidinyl) malonate and bis-[1-(butenyl-2)-2,2,6,6-tetramethyl-4-piperidinyl] malonate and bis-[1-(3-methyl-butenyl-2)-2,2,6,6-tetramethyl-4-piperidinyl] malonate and bis-[1-(4-tert.-butyl benzyl)-2,2,6,6-tetramethyl-4-piperidinyl] malonate, there are obtained respectively: bis-(1-benzyl-2,2,6,6-tetramethyl-4-piperidinyl) dibenzylmalonate (compound 11), m.p. 149°–150°, and bis(1-propyl-2,2,6,6-tetramethyl-4-piperidinyl) dibenzylmalonate (compound 12), m.p. 115°–116°, and bis-(1-butyl-2,2,6,6-tetramethyl-4-piperidinyl) dibenzylmalonate (compound 13), m.p. 124°–125°, and bis(1-hexyl-2,2,6,6-tetramethyl-4-piperidinyl) dibenzylmalonate (compound 14), m.p. 94°–95°, and bis-[1-(butenyl-2)-2,2,6,6-tetramethyl-4-piperidinyl] dibenzylmalonate (compound 15), m.p. 104°–105°), and bis-[1-(3-methyl-butenyl-2)-2,2,6,6-tetramethyl-4-piperidinyl] dibenzylmalonate (compound 16), m.p. 112°–113°, and bis-[1-(4-tert.-butylbenzyl)-2,2,6,6-tetramethyl-4-piperidinyl] dibenzylmalonate (compound 17), m.p. 151°–152°.

EXAMPLE 18

After the addition of 1 g of tetrabutyl-orthotitanate, 47 g of dimethyl diethylmalonate and 98.6 g of 1-allyl-2,2,6,6-tetramethyl-4-hydroxypiperidine in 100 ml of xylene are heated under a gentle stream of nitrogen to about 140°. The methanol forming during the reaction is continuously distilled off, and after about 6 hours the reaction is virtually completed. The reaction mixture is diluted with 200 ml of toluene, extracted three times with 100 ml of water each time, dried over sodium sulphate and concentrated by evaporation. Crystallisation of the residue from hexane yields bis-(1-allyl-2,2,6,6-tetramethyl-4-piperidinyl) diethylmalonate (compound 18), m.p. 135°–136°.

EXAMPLES 19–28

If there are used as starting products equivalent amounts of the corresponding dialkylated dimethylmalonates or diethylmalonates and of the alkylated -4-hydroxypiperidines, with the procedure being performed otherwise as described in Example 18, the following compounds are obtained: bis-(1-benzyl-2,2,6,6-tetramethyl-4-piperidinyl) diethylmalonate (compound 19), m.p. 158°–159°, and bis-(1-butyl-2,2,6,6-tetramethyl-4-piperidinyl) diethylmalonate (compound 20), m.p. 85°–86°, and bis-(1-benzyl-2,2,6,6-tetramethyl-4-piperidinyl) dimethylmalonate (compound 21), m.p. 144°–145°, and bis-(1-allyl-2,2,6,6-tetramethyl-4-piperidinyl) dibutylmalonate (compound 22), m.p. 68°–69°, and bis-(1-benzyl-2,2,6,6-tetramethyl-4-piperidinyl) dibutylmalonate (compound 23), m.p. 110°–112°, and bis-(1,2,2,6,6-pentamethyl-4-piperidinyl) ethyl-benzylmalonate (compound 24), m.p. 92°–93°, and bis-(1,2,2,6,6-pentamethyl-4-piperidinyl) n-butyl-benzylmalonate (compound 25), m.p. 78°–79°, and bis-(2,3,6-trimethyl-2,6-diethyl-4-piperidinyl) diethylmalonate (compound 26), b.p. 150°/0.005 mm Hg, and bis-(1-octyl-2,2,6,6-tetramethyl-4-piperidinyl) dibenzylmalonate (compound 27), m.p. 80°–81°, and bis-[1-(2-benzyloxyethyl)-2,2,6,6-tetramethyl-4-piperidinyl] n-butyl-benzylmalonate (compound 28) as a highly viscous undistilled oil.

EXAMPLE 29

131.6 g of bis-(2,2,6,6-tetramethyl-4-piperidinyl) diethylmalonate (compound 1) are stirred with 250 ml of acetic anhydride for 48 hours at 80°–85°. The excess anhydride and the acetic acid formed are then evaporated off as completely as possible in vacuo. The residual brownish oil is dissolved in 300 ml of toluene and the toluene solution is extracted with three times 100 ml of water. The toluene solution is dried over sodium sulphate and then completely evaporated. The crystalline residue is recrystallised from hexane. Bis-(1-acetyl-2,2,6,6-tetramethyl-4-piperidinyl) diethylmalonate (compound 29), which has a melting point of 112°–113°, is obtained.

EXAMPLES 30–31

If there are used according to Example 29, instead of bis-(2,2,6,6-tetramethyl-4-piperidinyl) diethylmalonate, a corresponding amount of bis-(2,2,6,6-tetramethyl-4-piperidinyl)di-n-butylmalonate and bis-(2,2,6,6-tetramethyl-4-piperidinyl) dibenzylmalonate, with the procedure otherwise being as described in Example 29, the following compounds are obtained respectively: bis-(1-acetyl-2,2,6,6-tetramethyl-4-piperidinyl) di-n-butylmalonate (compound 30) as a viscous yellowish oil (molecular distillation at 135°/0.005 mm Hg) and bis-(1-acetyl-2,2,6,6-tetramethyl-4-piperidinyl) dibenzylmalonate (compound 31), m.p. 132°–133°.

EXAMPLE 32

43.9 g of bis-(2,2,6,6-tetramethyl-4-piperidinyl) diethylmalonate (compound 1) are dissolved in 300 ml of toluene. A solution of 18 g of acrylic acid chloride in 50 ml of toluene is added dropwise to this solution at room temperature in 45 minutes and the mixture is then stirred for 3 hours at 60°. 22.3 g of triethylamine are now added dropwise to the reaction mixture in about 30 minutes and the mixture is then stirred for about 10 hours at 50°. After cooling to room temperature, triethylamine hydrochloride is filtered off and the toluene solution is completely evaporated. Crystallisation of the residue from ligroin gives bis-(1-acryloyl-2,2,6,6-tetramethyl-4-piperidinyl) diethylmalonate (compound 32) which has a melting point of 110°.

EXAMPLE 33

100 parts of polypropylene powder (Moplen, fibre grade, from Messrs. Montedison) are homogenised for 10 minutes at 200° C., in a Brabender plastograph, with 0.2 part of octadecyl β-(3,5-di-tert.-butyl-4-hydroxyphenyl)-propionate and 0.25 part of one of the stabilisers in the table which follows. The composition thus obtained is removed from the kneader as rapidly as possible and pressed in a toggle press to give a 2–3 mm thick sheet. Part of the resulting pressed blank is cut out and pressed between two high-gloss hard aluminium foils, using a manual hydraulic laboratory press, for 6 minutes at 260° and under a pressure of 12 tonnes to give a 0.5 mm thick sheet, which is immediately chilled in cold water. The 0.1 mm thick test sheet is produced from this 0.5 mm sheet under precisely the same conditions. 60×44 mm portions are now punched from this test sheet and exposed in the Xenotest 150. These test pieces are taken from the exposure apparatus at regular intervals and their carbonyl content is tested in an IR spectrophotometer. The increase in the carbonyl extinction on exposure is a measure of the photooxidative degradation of the polymer (see L. Balaban et al., J. Polymer Sci., Part C, 22, 1059–1071 (1969); J. F. Heacock, J. Polymer Sci., Part A-1, 22, 2921–34 (1969) and D. J. Carlsson and D. M. Wiles, Macromolecules 2, 587–606 (1969)) and, according to experience, is associated with a deterioration in the mechanical properties of the polymer. The time taken to reach a carbonyl extinction of about 0.3, at which the comparison sheet is brittle, is taken as a measure of the protective action.

The protective action of the stabilisers according to the invention can be seen from the table which follows:

TABLE

| Compound No. | Exposure time in hours until the carbonyl extinction is 0.300 |
| --- | --- |
| without a light protection agent | 1 400 |
| 1 | 16 300 |
| 2 | >10 000 |
| 3 | >3 000 |
| 7 | >10 000 |
| 8 | >10 000 |
| 19 | >3 000 |
| 24 | >3 000 |
| 25 | >3 000 |
| 29 | 12 000 |
| 30 | 9 000 |
| 32 | 11 000 |

What is claimed is:

1. A malonate of the formula I

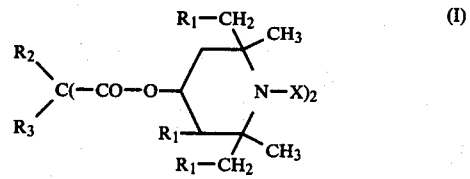

in which $R_1$ is hydrogen or $C_1$–$C_4$-alkyl, $R_2$ is $C_3$–$C_4$-alkenyl, benzyl or phenyl, cyano or phenyl substituted by $C_1$–$C_8$-alkyl or $C_1$–$C_8$-alkoxy, $R_3$ is $C_3$–$C_4$-alkenyl or benzyl and X denotes hydrogen, oxyl, $C_1$–$C_{12}$-alkyl, $C_3$–$C_6$-alkenyl, $C_3$–$C_4$-alkinyl, $C_2$–$C_{21}$-alkoxyalkyl, $C_7$–$C_{11}$-aralkyl, 2,3-epoxypropyl, an aliphatic acyl group selected from formyl, acetyl, acryloyl or crotonyl, or one of the groups —$CH_2COOR_4$, —$CH_2$—$CH(R_5)$—$OR_6$, —$COOR_7$ or —$CONHR_7$, in which $R_4$ is $C_1$–$C_8$-alkyl, $C_3$–$C_6$-alkenyl, phenyl, $C_7$–$C_8$-aralkyl or cyclohexyl and $R_5$ is hydrogen, methyl or phenyl and $R_6$ denotes hydrogen or acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, β-(3,5-di-t-butyl-4-hydroxyphenyl)propionyl, phenylacetyl, cinnamoyl or hexahydrobenzoyl and $R_7$ is $C_1$–$C_{12}$-alkyl, cyclohexyl, phenyl or benzyl.

2. A malonate according to claim 1, of the formula (I), in which $R_1$ is hydrogen or methyl, $R_2$ is allyl, methallyl, benzyl or phenyl, $R_3$ is allyl, methallyl or benzyl and X is hydrogen, oxyl, $C_1$–$C_8$-alkyl, $C_3$–$C_4$-alkenyl or alkinyl, $C_2$–$C_6$-alkoxyalkyl, $C_7$–$C_{11}$-aralkyl, acetyl, acryloyl or crotonyl or denotes one of the groups —$CH_2$—$COOR_4$, —$CH_2$—$CH(R_5)$ —$OR_6$, —$COOR_7$ or —$CONHR_7$, in which $R_4$ is $C_1$–$C_4$-alkyl, $C_3$–$C_4$-alkenyl, phenyl, $C_7$–$C_8$-aralkyl or cyclohexyl, $R_5$ is hydrogen, methyl or phenyl, $R_6$ is as defined in claim 15 and $R_7$ is $C_1$–$C_{12}$-alkyl.

3. A malonate according to claim 1, of the formula (I), in which $R_1$ is hydrogen or methyl, $R_2$ is allyl, methallyl, benzyl or phenyl, $R_3$ is benzyl and X is hydrogen, $C_1$–$C_4$-alkyl, allyl, benzyl, $C_2$–$C_6$-alkoxyalkyl, acetyl, acryloyl or crotonyl or one of the groups —CH$_2$—COOR$_4$, —CH$_2$—CH(R$_5$)—OR$_6$, —COOR$_7$ or —CONHR$_7$, in which $R_4$ is $C_1$–$C_4$-alkyl, $R_5$ denotes hydrogen or methyl, $R_6$ denotes hydrogen and $R_7$ is $C_1$–$C_4$-alkyl.

4. A malonate according to claim 1, of the formula (I), in which $R_1$ is hydrogen or methyl, $R_2$ is allyl, methallyl or benzyl, $R_3$ is benzyl and X is hydrogen, methyl, allyl, benzyl or acetyl.

5. A malonate according to claim 2, in which X is benzyl substituted by $C_1$–$C_4$-alkyl.

6. A malonate according to claim 1, namely bis-(1,2,2,6,6-pentamethyl-4-piperidinyl) dibenzylmalonate.

7. A malonate according to claim 1, namely bis-(1,2,2,6,6-pentamethyl-4-piperidinyl) diallylmalonate.

8. A malonate according to claim 1, namely bis-(1-allyl-2,2,6,6-tetramethyl-4-piperidinyl) dibenzylmalonate.

9. An organic material ordinarily subject to light- or thermal-induced degradation containing a malonate of claim 1 in amounts sufficient to stabilize the material against said degradation.

10. An organic material according to claim 9, wherein the malonate is present in amounts of from 0.01 to 5% by weight, based on the weight of the material to be stabilized.

11. An organic material according to claim 9, wherein the organic material is a polymer.

12. An organic material according to claim 11, wherein the polymer is selected from the group consisting of a polyolefin, a styrene or a polyurethane polymer.

13. A method of stabilizing an organic material ordinarily subject to light- and thermal-induced degradation which comprises adding to the organic material a stabilizing amount of a malonate of claim 1 to prevent said degradation.

14. A method according to claim 13, wherein the malonate is added in an amount of 0.01 to 5% by weight, based on the weight of the organic material to be stabilized.

15. A method according to claim 13, wherein the organic material is a polymer.

16. A method according to claim 15, wherein the polymer is selected from the group consisting of a polyolefin, a styrene of a polyurethane polymer.

* * * * *